United States Patent [19]
Heilman et al.

[11] Patent Number: 5,569,181
[45] Date of Patent: Oct. 29, 1996

[54] STERILITY ASSURANCE FOR CONTRAST DELIVERY SYSTEM

[75] Inventors: Marlin S. Heilman, Sarver; Arthur E. Uber, III, Pittsburgh, both of Pa.

[73] Assignee: Medrad, Inc., Pittsburgh, Pa.

[21] Appl. No.: 144,845

[22] Filed: Oct. 28, 1993

[51] Int. Cl.⁶ .................................................... A61J 3/00
[52] U.S. Cl. ................................................ 604/30
[58] Field of Search .................... 128/654, 655, 128/DIG. 12, DIG. 13; 604/65–67, 82, 83, 246, 51, 247, 30, 131, 157, 404, 407

[56] References Cited

U.S. PATENT DOCUMENTS

| | | |
|---|---|---|
| 3,349,713 | 10/1967 | Fassbender . |
| 3,898,983 | 8/1975 | Elam . |
| 3,968,195 | 7/1976 | Bishop . |
| 4,199,000 | 3/1980 | Edstrom . |
| 4,223,675 | 9/1980 | Williams . |
| 4,340,153 | 7/1982 | Spivey . |
| 4,434,822 | 3/1984 | Bellamy et al. . |
| 4,479,760 | 10/1984 | Bilstad et al. . |
| 4,479,761 | 10/1984 | Bilstad et al. . |
| 4,479,762 | 10/1984 | Bilstad et al. . |
| 4,563,175 | 1/1986 | LaFond . |
| 4,585,009 | 4/1986 | Barker et al. ............................ 128/655 |
| 4,610,670 | 9/1986 | Spencer . |
| 4,610,790 | 9/1986 | Reti et al. . |
| 4,634,426 | 1/1987 | Kamen . |
| 4,636,144 | 1/1987 | Abe et al. . |
| 4,750,643 | 6/1988 | Wertrich . |
| 4,783,273 | 11/1988 | Knutsson et al. . |
| 4,835,521 | 5/1989 | Andrejasich et al. . |
| 4,857,056 | 8/1989 | Talonn . |
| 4,879,880 | 11/1989 | Harrison . |
| 4,925,444 | 5/1990 | Orkin et al. . |
| 4,943,279 | 7/1990 | Samiotes et al. . |
| 4,946,439 | 8/1990 | Eggers . |
| 4,950,245 | 8/1990 | Brown et al. . |
| 4,978,335 | 12/1990 | Arthur, III . |
| 4,981,467 | 1/1991 | Bobo, Jr. et al. . |
| 5,009,654 | 4/1991 | Minshall et al. . |
| 5,059,173 | 10/1991 | Sacco . |
| 5,100,380 | 11/1992 | Epstein et al. ............................ 604/67 |
| 5,207,642 | 5/1993 | Orkin et al. . |
| 5,230,614 | 7/1993 | Zanger et al. . |
| B1 5,009,654 | 7/1993 | Minshall et al. . |

FOREIGN PATENT DOCUMENTS

| | | |
|---|---|---|
| 2045070 | 2/1992 | Canada . |
| 41 21 568 A1 | 10/1992 | Germany . |

*Primary Examiner*—Manuel Mendez
*Attorney, Agent, or Firm*—Keck, Mahin & Cate

[57] ABSTRACT

Apparatus and process for injection of a multiple number of patients with a sterile fluid while assuring sterility by providing devices which control the fluid flow in such ways that injection devices are isolated from each other, as well as from the source of sterile fluid, such as by use of selective valving devices and disposable dosing units.

10 Claims, 6 Drawing Sheets

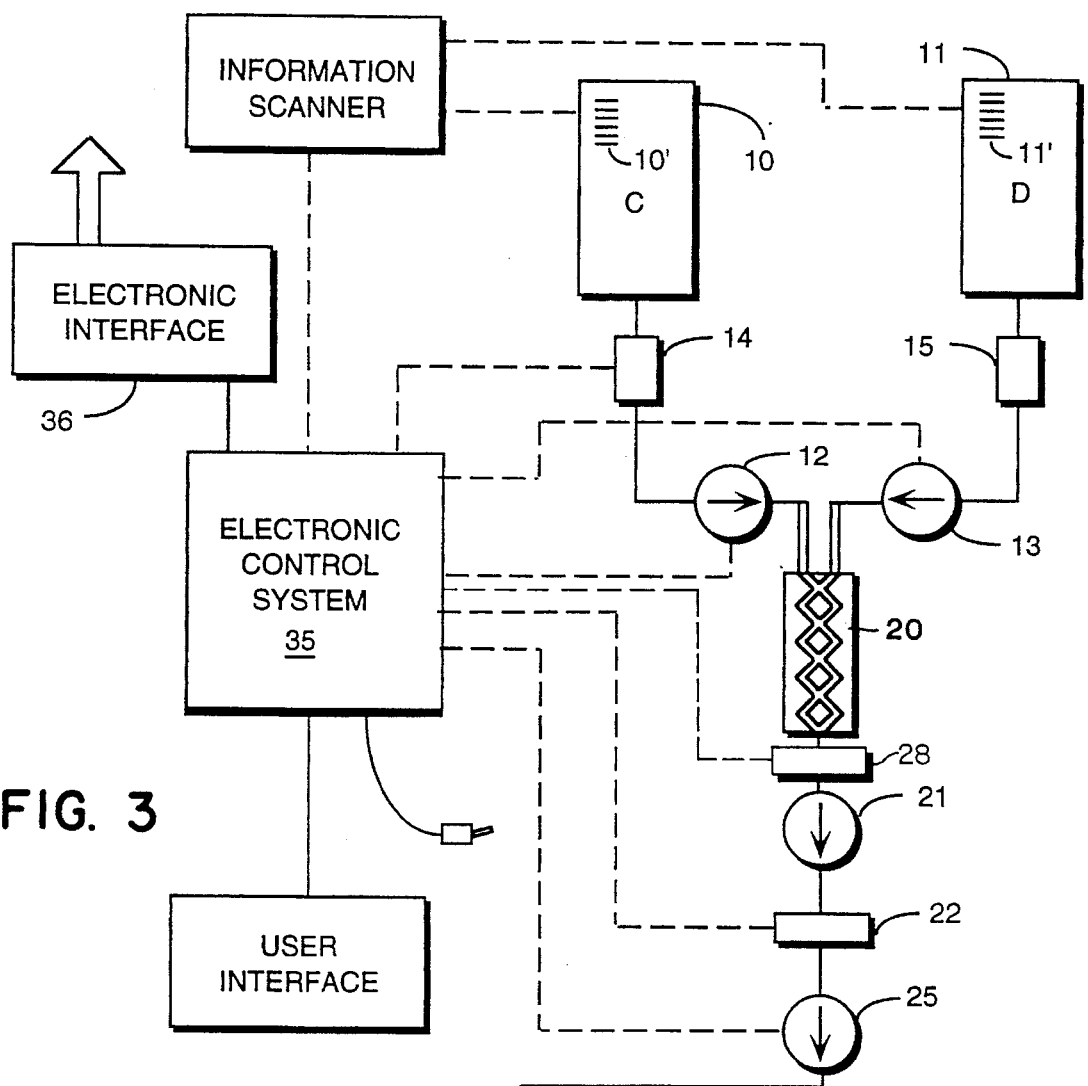
FIG. 3
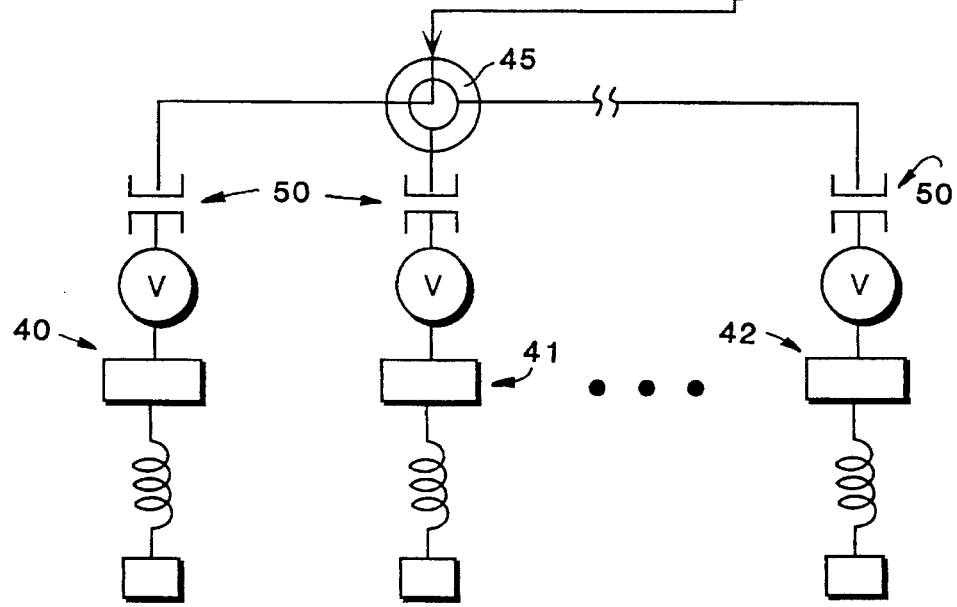

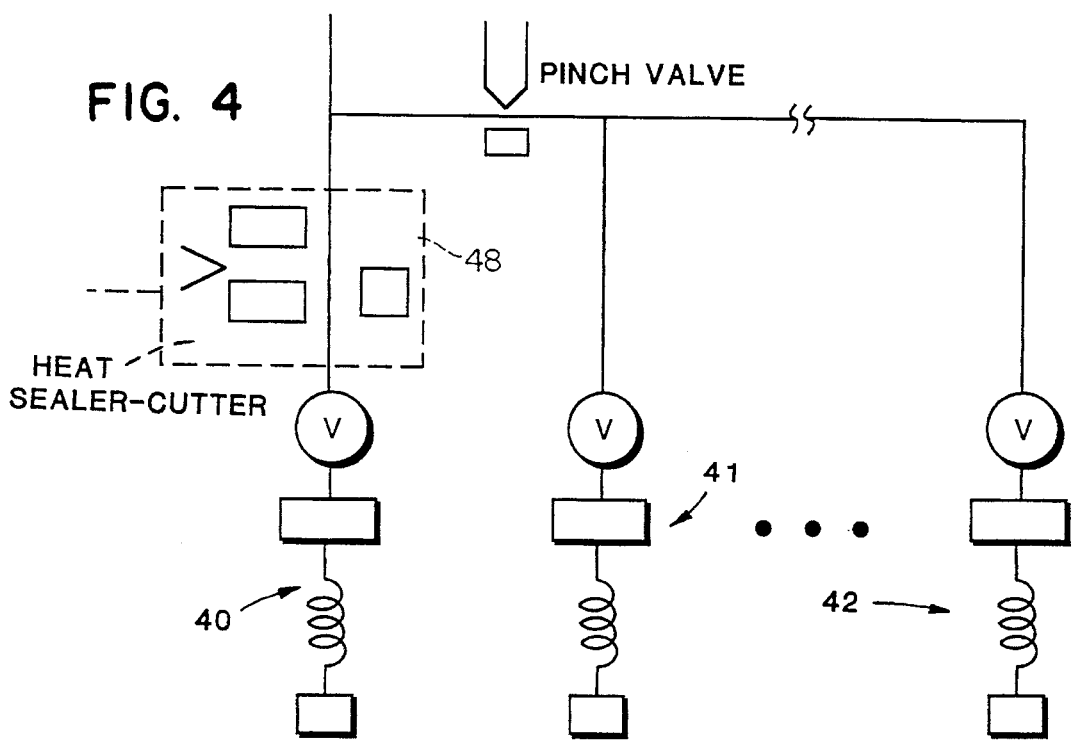
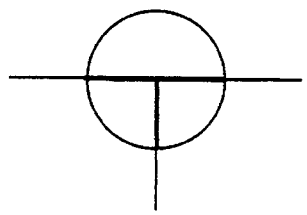
FIG. 5A
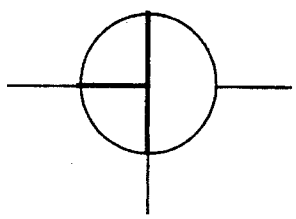
FIG. 5B
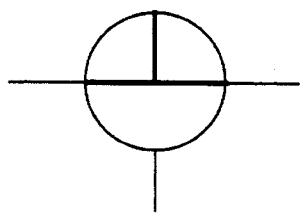
FIG. 5C
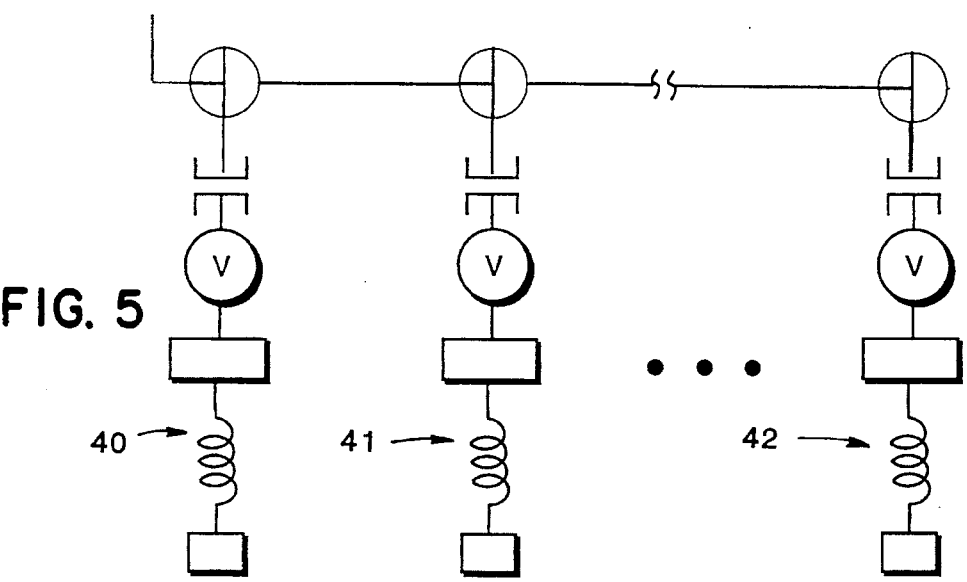

STERILITY ASSURANCE FOR CONTRAST DELIVERY SYSTEM

BACKGROUND OF THE INVENTION

Contrast media are used in many medical diagnostic and therapeutic imaging procedures. Diagnostically these include X-ray procedures for instance, angiography, venography and urography, CT scanning, magnetic resonance imaging [MRI], and ultrasonic imaging. Contrast media is used during therapeutic procedures such as angioplastic and other interventional radiologic procedures. Because this contrast material is injected into the patient, it must be sterile and contain a minimum of pyrogens.

Presently, most contrast is provided in sterilized glass bottles, ranging in size from 20 ml to 200 ml. Plastic packages are also available. Non-ionic X-ray contrast media is expensive, on the order of $1/ml. Ionic contrast media costs about $0.10/ml. Non-ion contrast has fewer complications but because of the cost, it is not universally used. MRI contrast costs about $5/ml. All the containers are single use, which means that once a bottle is opened, it should be used for that patient or thrown away, although a multi-use 1,000 ml bottle has been recently approved by the FDA.

A hospital must purchase and stock many concentrations in multiple bottle sizes to provide the right amount of the right concentration for a specific procedure, while minimizing the wastage of contrast remaining in any opened bottles.

This multitude of sizes and concentrations increases costs throughout the contrast supplier chain. Manufacturers need to make many batches with various concentrations, and package each in many sizes of bottles. They must have inventories of each on hand to quickly meet the customer's request. Each concentration and size entails an added regulatory burden.

In the hospital, there are additional costs due to the work purchasing the various brands and sizes, storage space is required for stocking, cabinets are required in each procedure room, and time is required to make sure the right numbers of each bottle are kept in each room. Frustration, waste and/or less than optimal studies can occur if this complex logistics chain fails at any point.

To illustrate the problem, consider a manufacturer who makes 5 concentrations of contrast, packages them in bottles of 10, 25, 50, 75, 100, 150 and 200 ml. The manufacturer now has 35 different products to get approval for, schedule production for, maintain sufficient stock of, and finally, ship to his customers.

Presently, most hospitals utilize a standard protocol for a given set of indications. For instance, for a CT scan of the liver, the protocol may call for 130 ml of contrast injected at 3 ml/s. This protocol is used for a wide variety of patient weights and physical conditions. One goal of this standardization is to minimize air errors. Another is to decrease the likelihood of having to repeat the procedure, with the problem of additional radiation and contrast dose to the patient.

However, there are costs associated with this method. Many patients may get more contrast than they need for an image to be diagnostic. Overdosing wastes contrast, but there is no way with the present contrast supply and delivery system to remedy this, without stocking many more sizes of bottles and working harder to fill syringes. Other patients may have studies that are less than optimum. They do not receive enough contrast. The contrast that isn't used doesn't cost anything, but there is a much greater risk of having to repeat the whole procedure, with a much greater cost than a few milliliters of contrast. Again, using many bottle sizes and a cumbersome filling procedure is the only solution presently available.

In angiography, there are not set protocols to the same extent as in CT, because patient size determines vessel size which in turn determines the volume and flow rate needed. This means that a fixed amount of contrast cannot be prepared ahead of time with any confidence that more won't be needed during the procedure or that a significant amount won't remain and be wasted at the end of the procedure. To avoid delays while working on the patient, the technician loads more than the average amount used, with the realization that some is likely to be wasted, and there still is a chance that a delay will occur when more has to be loaded.

Another problem this system addresses is the volume and cost of items which must be disposed of after each patient. To save contrast, several small glass bottles may be opened per patient. One or more plastic syringes, and various tubing arrangements are used. There is a cost to purchase and a cost to dispose of each of these items.

The problems arising from the use of a multiplicity of concentrations and container sizes was addressed in German DE 4121568A1. In this disclosure, it was provided a supply tank of contrast agent which could contain from about 0.1 to as much as 100 liters. The device also included a similar tank that contained a diluent so that the composition of the concentrate could be varied to form a variety of concentrations. The abstract in the German patent utilizes a bulk mechanical mixer with sequential flow and so it would not seem to provide for the production of continuously variable concentrations. Nor, and importantly, is there any description of means to prevent cross-contamination when the apparatus is used sequentially on a plurality of patients. Sterility is provided by active sterilization by steam or chemicals. This requires considerable additional hardware and heat resistant materials; or there must be additional safeguards to prevent any sterilizing fluid from being injected.

Machines for mixing IV solutions also do not connect directly to the patient. Generally, the controls require that the operator know which fluid is in which position and that he choose the mixing ratios. In U.S. Pat. No. 4,341,153, medication is diluted and delivered to a syringe. There are no means described for connection to a patient, there is no mixing means and only sequential flows are described.

U.S. Pat. No. 4,610,790 describes in great detail how to make sterile water for diluting medications. Making diluted fluids is mentioned in little detail. U.S. Pat. No. 4,783,273 describes the use of sterilizing filters to assure the sterility of bulk fluids. Concentration monitors are also described. A serious drawback is the use of chemical sterilants.

In none of the references mentioned above is a mechanism described which can be used to sequentially or simultaneously inject contrast into several patients while minimizing the chance of cross-contamination and assuring sterility. Nor is there any mention of information integrity or information transfer so that the proper procedures are followed with the diluted medications.

OBJECTS OF THE INVENTION

It is a principal object of this invention to provide an improved apparatus and method for assuring sterility in multi-patient contrast delivery systems which may be used over the course of hours or days.

It is another object of this invention to provide a system with improved sterility assurance both before and during use.

Other objects and advantages of this invention will be in part obvious and in part explained by reference to the accompanying specification and drawings in which:

FIG. 1 diagrammatically shows an apparatus and a system for utilizing bulk contrast and diluent solutions which permit use in conjunction with multiple patients.

FIG. 3 is a diagrammatic view showing yet another form of attaining system sterility.

FIG. 4 is another alternative illustrating a system of attaining system sterility.

FIG. 5 is yet another diagrammatic showing of an overall contrast to system showing a modified means for assuring system sterility.

FIGS. 5A, 5B and 5C are diagrammatic views of alternative positions of a stop cock shown in FIG. 5.

DESCRIPTION OF THE INVENTION

Figure 1:
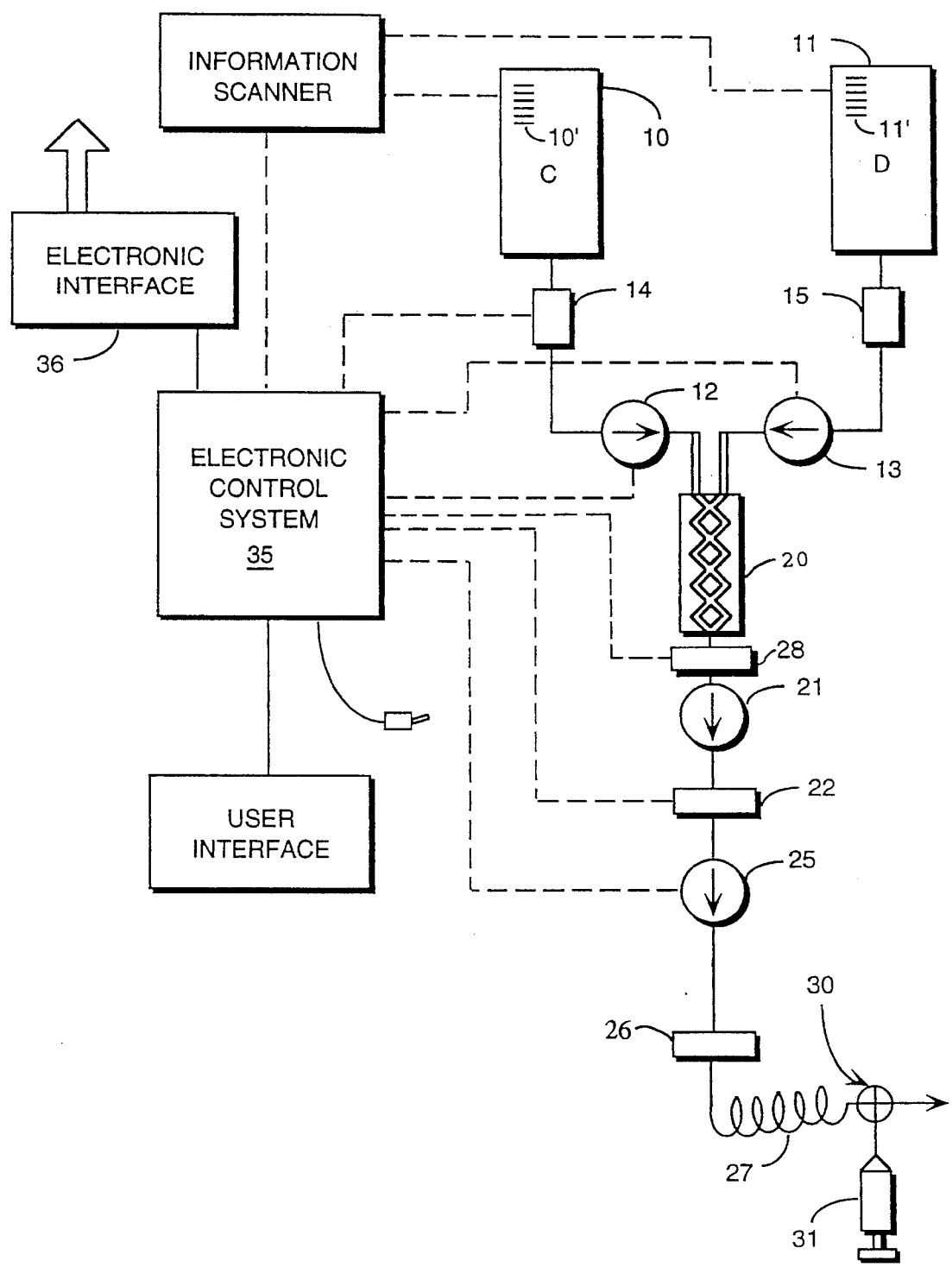

Referring to FIG. 1 of the drawings there is shown an overall system similar to that disclosed in applicant's copending application Ser. No. 08/144,462 which was filed of even date herewith and assigned to the same assignee as the present application. In this figure, numeral 10 indicates a source of contrast medium which is in the form of a bulk container. Numeral 11 represents a similar container that is used to hold a supply of diluent, in the event that it is desired to reduce the concentration of the contrast medium contained within source 10. The containers may be rigid or flexible, glass or a fluid compatible plastic such as polypropylene. If the containers are rigid one of many known methods is used to vent the container with sterile air. A non-vented collapsible container is preferred to avoid air entry. A metering pump 12 draws contrast from the contrast supplied from source 10 at the proper flow rate. The second metering pump 13 draws diluent (when desired) from the bulk reservoir 11 within which the supply of diluent is contained. A preferred metering pump is a precision peristaltic pump with santopreen tubing. A wall design similar to that of U.S. Pat. No. 5,230,614 would minimize the pulsatile flow characteristics. As the fluids are removed from the containers 10 and 11, they are heated by means of the heaters 14 and 15 so that they approximate body temperature. The heating, of course, decreases the viscosity of the contrast and makes the fluid more comfortable for the patient (rather than in-line heaters, the bulk containers could be heated).

Upon leaving the metering pumps 12 and 13 the fluids meet as they are joined and they flow through a static mixer 20 that contains helical vanes. The company ConProTec makes many sizes and lengths, some with polypropylene vanes and case. These static mixers are designed for mixing fluids with very different viscosities and varying dilution ratios. The exact length and diameter to be used will depend to some degree upon the viscosity of the contrast, dilution ranges and flow rates. The flow can be next through a concentration monitor 28. This is optional but serves a useful verification function. The monitor measures a property which changes with concentration, such as electrical conduction, optical refraction index, rotation of polarized light, attenuation of sound, speed of sound, density, viscosity or pressure drop through a fixed section. The mixture next flows through a back-flow prevention valve 21 which can be either a spring loaded ball valve or duck billed valve. This is an important feature of the overall device since it helps prevent cross contamination when the device is used on subsequent patients. By including valve 21 in the system, it is possible for fluid to flow only in one direction and there is not a chance that contaminated fluid can be drawn back into the bulk fluid reservoirs from the patient's body.

Next, the fluid flows through a fluid assurance detector 22 which may be an ultrasonic detector so that the presence or absence of air in the fluid can be determined. Since these types of devices cannot detect small air bubbles, by being located before the pressurization pump 25, bubbles will be as large as possible. It helps minimize the chance that a broken line or human error can inject air into the patient.

Up until this point, the flow of the liquid has been at relatively low pressures. To inject the fluid through the connector tube 27 and the catheter into the patient, relatively high pressures are needed. Presently this procedure is done by powerful syringe pump, but these have the drawback that they can only inject one syringe full at a time. In the present embodiment, the pressurizing pump 25 is a gear pump, with the housing and gears made from TPX, which is a polymethylpentene plastic made by Mitsui, Inc. of Japan. The parts can optionally be polycarbonate or teflon coated polycarbonate. This gives the clarity needed to check for bubbles, and the drug compatibility of teflon. The shaft of the gear pump is connected to an electric motor with a spline or other removable mechanism so that the pump head can be disposed of when required.

The pressurized fluid flows through a 0.2 micron "sterilizing" filter 26. These filters are becoming a standard way to assure sterility of the solution. Its purpose here is to prevent migration of any bacteria from the patient into the pump. In cooperation with the backflow valve, cross contamination is minimized. A flexible connector tube 27 carries the fluid to the patient. These tubes are commercially available, usually made out of PVC. This component is disposed of after each patient use so that it does not need to have long term compatibility with contrast medium.

At the patient, there is a three way stop cock 30 and a hand syringe 31. These items can be used for several things, such as to aspirate blood and thus verify good IV catheter placement in CT. Syringe 31 can be used to inject other medications. It can also be used to fill a hand syringe which can be removed and used for test injections during angiography. With one position of the stop cock the fluid flows straight into the patient.

The apparatus includes an electronic control system (ECS) 35 to assure that the needs of the patient are met safely. ECS 35 gets information on the contents of the bulk reservoirs 10 and 11. The preferred method is to read bar codes indicated by numerals 10' and 11' respectively. Another way is to quiz the operator to enter the data each time a bulk reservoir is changed, and then store that information. The operator would read the label on or packaged with the bulk reservoir, and enter the appropriate data. This need only be done when a bulk reservoir is changed.

With each injection, the operator needs to tell the system what to do. The data most similar to present practice is: 1)

the concentration desired, 2) the flow rate, and 3) the total volume to be delivered. Present practice also includes multiple phases with various flow rates during each phase. This system would allow various contrast concentrations during each phase as well.

Figure 2:
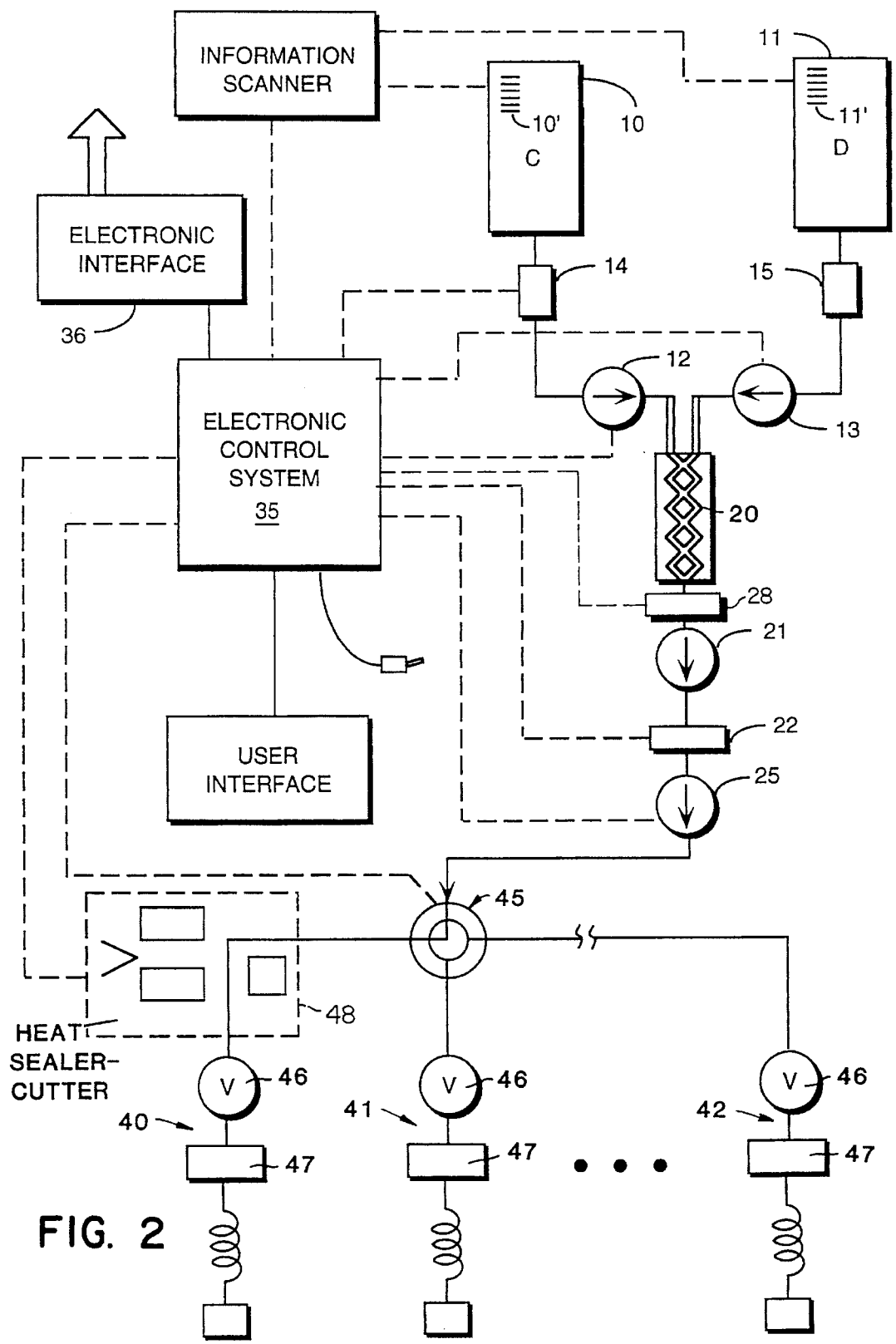
FIG. 2 is a diagram similar to FIG. 1 which illustrates one form of assuring system sterility.

However, given the capabilities of this system, a preferred set of information is: 1) the procedure being done, and 2) the patient weight. This way the contrast dose could be optimized for the patient. The algorithm would have been previously provided information on milligrams of iodine per kilogram of patient for each procedure when the system was first installed in the hospital. It could display concentration, flow rate and volume for operator verification, if the operator desired. An electronic interface 36 is shown which can connect to the hospital information system to get information on the patient, such as weight. Then the operator would only have to input the patient identification number. The electronic interface could also be connected to the imaging equipment. It could send or receive information so that, for instance, the operator only needs to program the CT scanner with number of slices and body section, and this would be transmitted to the contrast delivery system to be used in determining flow rates and delays. The electronic interface would also be used to let the scanner trigger the contrast delivery system or vice versa, after the appropriate delays. A hard copy printer may be optionally part of the user interface, receiving data from the ECS. This can print a record of the actual injection for insertion into the patient records. The output may be alphanumeric or be a graphical representation of the injection. Referring now to FIG. 2, the overall system is similar to that described in connection with FIG. 1 except that the system for assuring sterility is different. In this case, the source of sterile treatment fluid, which are the reservoirs 10 and 11, are operably connected by the fluid connection through the static mixer 20, backflow prevention valve 21, etc. to means for selectively controlling the manner in which fluid is introduced into a plurality of disposable patient dosing units 40, 41, and 42. After the pressurizing pump 25 the fluid path leads to a rotary valve 45. This valve can connect the input line from the pressurizing pump to any one of the identical elongated flexible dosing units. Each dosing unit, in the configuration shown in FIG. 2, is in actuality a length of tubing and contains a backflow prevention valve 46 and a sterile filter 47 to prevent reverse contamination or cross contamination of the fluid path by the patient.

There are many ways for sterility to be compromised. Sterility can be compromised any time sterile parts are exposed to unfiltered air. This involves the smallest (but greater than zero) probability of contamination: most "sterile" connections made in a hospital involve a needle piercing a rubber septum, both of which have been exposed to room air. This is the best technique that is available at the present time. However, problems do result, as is evidenced by the development of ultraviolet connection sterilizers for peritoneal dialysis.

Touching a sterile surface with anything except another sterile surface is a more serious form of contamination. Almost any connection made by the operator can have this inadvertently happen.

Cross contamination is a third form of sterility compromise. It refers to pathogens from one patient contaminating the system and potentially being passed on to another patient. It is very significant because it is impossible to not contact the patient. Cross contamination is being discussed more fully in co-pending application Ser. No. 08/144,460 filed of even date herewith and assigned to the same assignee as the present invention.

The fluid path in FIG. 2 is preferably provided from the manufacturer fully connected and sterile. In this embodiment, the fluids are isolated from the remainder of the fluid path. Minshall in U.S. Pat. No. 5,009,654 shows several ways of accomplishing this. Or the fluid path may be separate from the bulk reservoirs as described in copending application Ser. No. 08/144,462. The connections may be made using a sterile technique such as ultraviolet illumination or heated membrane rupture. Before the first patient is injected utilizing the device shown in FIG. 2, the seals of the fluid reservoirs are broken, and the fluid is pumped throughout the fluid path. Because of the cost of contrast, it is pumped only to the beginning of the mixer 20. Then diluent or flush is used to push air from the remainder of the fluid path including the first dosing unit 40. The air will remain in the other dosing units. Now the system is ready for use for the first injection. After the injection, separation is made of the disposable unit 40. To preserve the sterility, as shown in FIG. 2, the tube comprising the disposable unit is sealed in two places and is then cut between the two heat seals. This has the benefit of closing the end of the disposable unit so that fluid doesn't leak out and it seals the system fluid path sterilely. There are many alternatives to this method of sealing which are not shown in FIG. 2, for example ultrasonic welding or RF heating could also be used. The tubing could be crimped and held closed by a metal band before cutting. Any permanent sealing method would suffice. There could be for example, a connector which is disconnected after sealing, so that no cutting is needed. By following this method of sealing ends it is possible to fill each dosing unit 40, 41 and 42 in sequence and thereby sterily isolate each unit both from the fluid sources 10, 11 and from succeeding dosing units. While the present practice is to separate and dispose of each dosing unit, it is possible with this apparatus to just isolate the dosing unit and place it in a bag or other container associated with the apparatus. Then the entire fluid path can be disposed of at one time. Thus disposable dosing units do not have to be individually disposed of.

FIG. 3 illustrates a method in which heat sealing of each of the disposable dosing units is eliminated. If the rotary valve is only able to operate in one direction, using ratchets or the like, then simply rotating the valve to the next position is sufficient to maintain sterility. After rotation the connections 50 to the per patient disposable dosing units can simply be opened. These connections could be similar to those in self sealing fluid connectors to prevent dripping from the disposable dosing units 40, 41 and 42, if desired.

It is possible to make the rotary valve 45 of FIG. 3 be controlled by the ECS 35, or be manual as shown in FIG. 2. Disconnecting the disposable dosing unit could also be automatically controlled. The trade off is the amount of operator vigilance required and chance for error versus the increase in mechanical complexity and its impact on reliability. A number of rotary valves may be used, if many dosing units are needed.

FIG. 4 shows an alternative embodiment where the rotary valve system is replaced with static closures. The advantage of this system is that the whole fluid line is normally open, as compared to the rotary valve where many fluid lines are sealed off. A section of the fluid line is inserted into a pinch valve on the durable (that is reusable) section of the system. This insures that fluid only flows to the first disposable dosing unit 40. Heat sealing and cutting is shown by way of example, as the means 46 of closing the system. Before use on the next patient, the operator moves the pinch valve so it lets fluid flow to the next tube in line, but no further.

The fluid path may be sterilized when full of air through use of many methods. An added benefit of the device of FIG. 4 is the ability to totally fill the fluid path with fluid, preferably with diluting or flushing fluid, and eliminate any gas. The contrast would still be sealed in a separate, but sterilely connected chamber. Because the fluid path openly communicates its full length, it is possible to pull a vacuum on the disposable dosing unit, fill it with liquid, and then connect it to the bulk containers. The entire fluid filled assembly can now be sterilized.

FIG. 5 shows a configuration similar to FIG. 4 except that there is a stop cock at each junction of the durable tube and the dosing units. Each stop cock has three positions. In the first position, shown in FIG. 5A all lines can be made to communicate as in the arrangement of FIG. 4, so it has the same capability. After sterilization and filling, all valves are rotated 90 degrees clockwise to the configuration shown in FIG. 5B. Now they can be used one at a time. After use the valve is rotated 90 degrees clockwise to the configuration in FIG. 5C sealing the system from outside contaminants and enabling fluid to flow to the next position.

Figure 6:
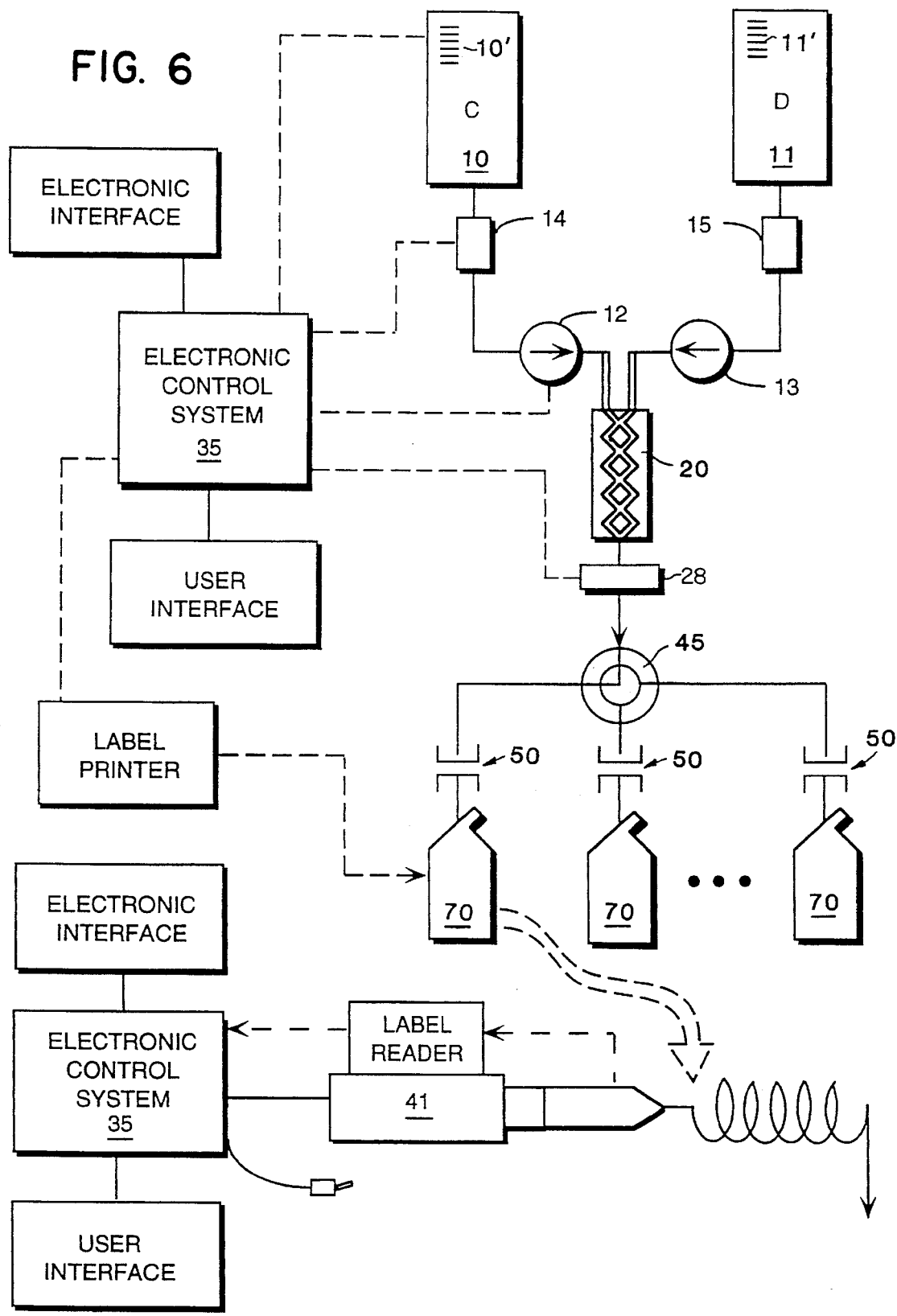
FIG. 6 is a diagram showing a modified form for assuring system sterility.

FIG. 6 shows the present concept applied to filling another form of multiple dosing units. The fluid path from the manufacturer includes many dose containers 70 attached and sterilized. When a patient is to be treated, a dose container 70 is filled and removed from the system. The embodiment shows the one way latching rotary valve 45, but any of the fluid paths previously described would also work.

Figure 7:
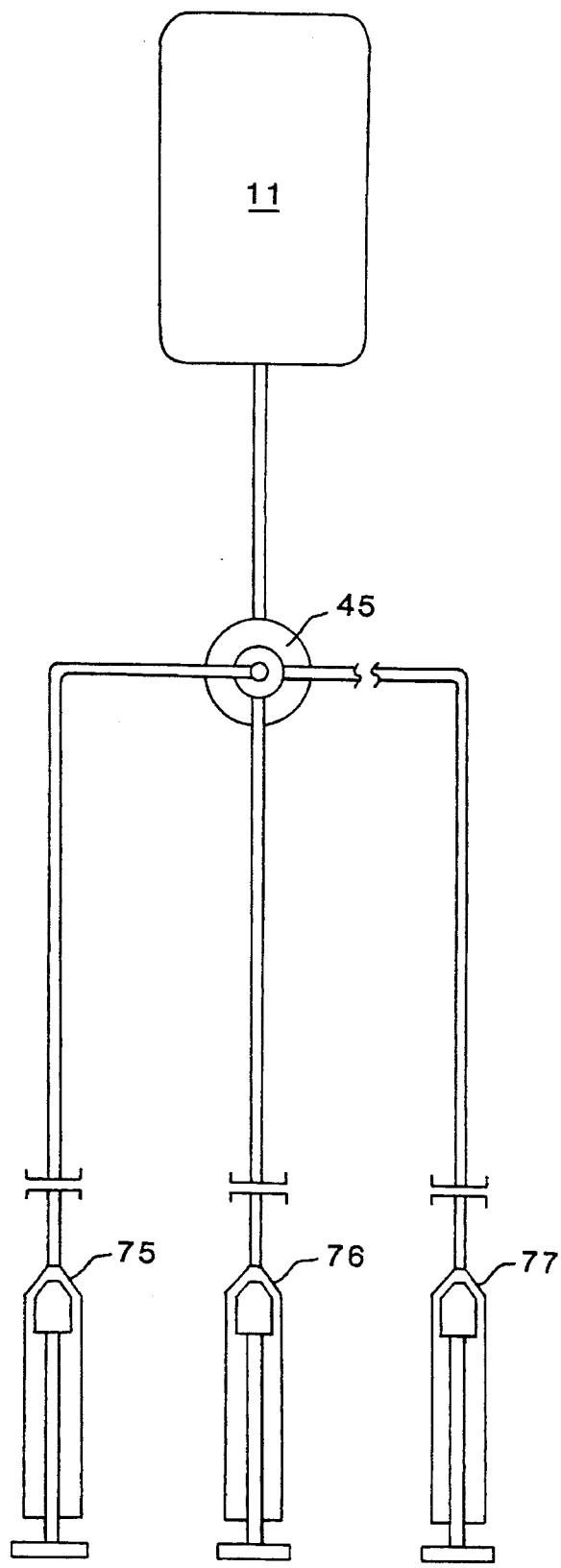
FIG. 7 is a diagrammatic showing of a still further form of assuring system sterility.

A simplified system using the inventive concept illustrated in FIG. 6 is shown in FIG. 7. Here there is just one reservoir 11 of fluid. This reservoir can be flexible or have a vent to admit air. The whole system is assembled and sterilized by the manufacturer. When put into use the connection to the bulk reservoir is made by piercing a seal. Many ways of doing this are taught by Bellamy and U.S. Pat. No. 4,434,822. Gravity feeds the fluid to the rotary valve 45. The plunger of a first syringe (disposable dosing unit) 75 is moved backwards by hand to pull the fluid into it. When the desired amount of fluid is withdrawn, the rotary valve is turned to the next position and the syringe is removed. Subsequently, additional dosing units 76 and 77, etc., can be filled, removed until needed. It is a useful feature to design the rotary valve so that the syringe cannot be removed until the valve is turned, preventing human error from contaminating the system. More syringes would be attached than would be needed, but the wastage of syringes would be less than the savings over individual use medication packaging and wasted medication.

It is also possible to package the syringes with the plungers at the back so that air is first forced into the bulk reservoir bottle from the syringe, and then fluid flows into the syringe as the plunger is withdrawn.

It is possible, although not shown in a figure, for there to be no bulk container. Some syringes could be full of fluid and some could be empty. They are connected through a valving arrangement similar to that shown in 5A. When the first syringe is to be used, any extra fluid from it is pushed into one of the empty syringes. Then the valve on the first syringe is sealed and the first syringe is removed. This is repeated for subsequent syringes, with excess fluid being used to fill empty syringes. It is likely that there will be empty syringes remaining when all the fluid is finally used. This waste of plastic is acceptable because the fluid is much more expensive. This process can be done manually or automatically.

Figure 8:
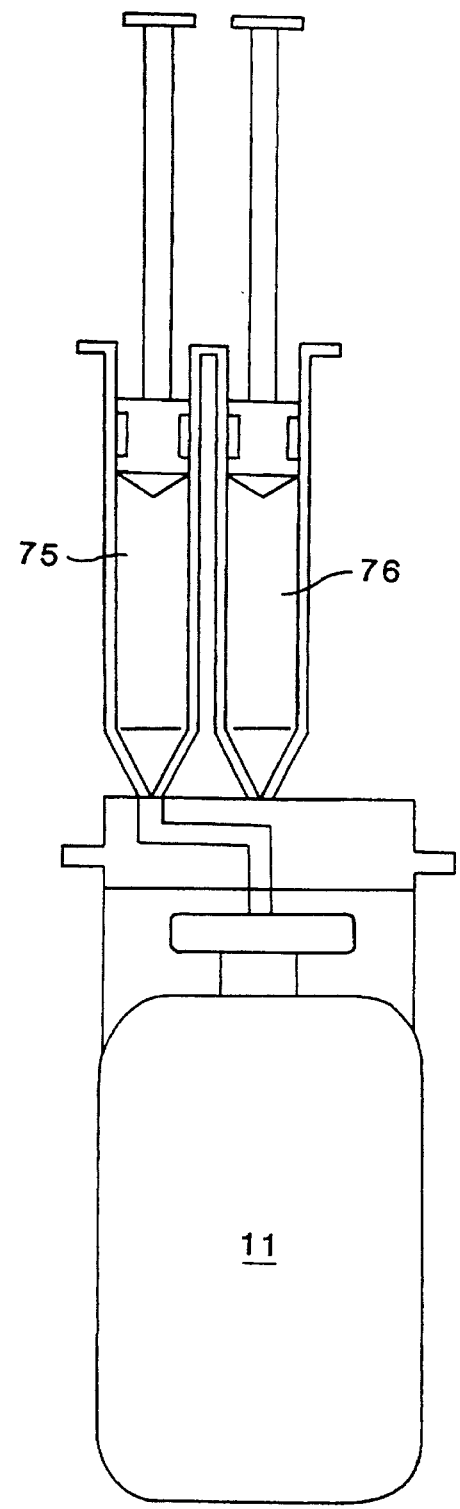
FIG. 8 is a diagrammatic showing of a compact system for assuring system sterility.

It is also possible for the dosing unit syringes to be above the bulk reservoir 11, and in this configuration would make a compact arrangement for use in a doctor's office, as shown for example in FIG. 8. The primary savings in using this modification will be from being able to use only the exact volume of fluid needed for the individual patient.

The embodiments presented above are those preferred by the inventors, but it is possible for those skilled in the art to devise modifications and changes all of which fall within the purview of the appended claims. The present description is given by way of example and is not intended to be limiting to the scope of the invention described and claimed.

What is claimed is:

1. An apparatus for injecting a plurality of successive patients with a treatment fluid, comprising:

(a) a source of sterile treatment fluid;

(b) an assembly of at least two preconnected sterile disposable patient dosing units;

(c) connectors for providing fluid connection between said source of treatment fluid and each said assembly of disposable patient dosing units;

(d) means for selectively controlling said connectors for enabling fluid flow in one direction only, and for filling said dosing units only in sequence; and (e) means for isolating each dosing unit from said fluid source and from succeeding dosing units after use.

2. An apparatus as defined in claim 1 wherein said means for selectively controlling said connectors comprises a rotary valve operable in one direction only.

3. An apparatus as defined in claim 1 wherein at least one of said dosing units comprises an elongated flexible tube, back flow preventing means and a sterile filter.

4. An apparatus as defined in claim 1 wherein said disposable patient dosing units comprises a syringe.

5. An apparatus as defined in claim 1 wherein said selective controlling means comprises separate valves positioned to selectively control operation of each of the plurality of disposable dosing units.

6. An apparatus as in claim 1 where the source of sterile treatment fluid and the plurality of sterile disposable dosing units are preassembled by the manufacturer.

7. An apparatus according to claim 1, wherein at least two of said patient dosing units are preconnected with said source of sterile treatment fluid.

8. An apparatus as defined in claim 1, wherein said means for selectively controlling said connectors comprises valve means.

9. In a process of injecting in series a plurality of patients with sterile treatment fluid, the steps comprising:

(a) providing a source of sterile treatment fluid;

(b) providing a plurality of preconnected sterile fluid patient dosing units operably connected to the source of sterile fluid;

(c) utilizing a first of the dosing units and injecting the fluid into a patient;

(d) isolating the first of the dosing units from the source of sterile fluid; and (e) thereafter in sequence utilizing each of the remaining dosing units, injecting a patient and isolating each unit so used from the source, until either the fluid is consumed or all of the mutually exclusive fluid dosage units are consumed.

10. A process for injecting a plurality of successive patients with a treatment fluid, comprising:

(a) providing a source of sterile treatment fluid;

(b) providing an assembly of at least two preconnected sterile disposable patient dosing units;

(c) providing fluid connectors between said source of treatment fluid and each said assembly of disposable patient dosing units;

(d) using at least one valve for selectively controlling said fluid connectors to fill said dosing units only in sequence; and (e) isolating each dosing unit from said fluid source and from succeeding dosing units after use.

* * * * *